United States Patent [19]
Hulls

[11] 3,955,318
[45] May 11, 1976

[54] WASTE PURIFICATION SYSTEM

[75] Inventor: John Robin Hulls, Mill Valley, Calif.

[73] Assignee: Bio-Kinetics Inc., San Rafael, Calif.

[22] Filed: Mar. 5, 1975

[21] Appl. No.: 555,458

Related U.S. Application Data

[63] Continuation of Ser. No. 342,516, March 19, 1973, abandoned, which is a continuation-in-part of Ser. No. 205,152, Dec. 6, 1971, abandoned.

[52] U.S. Cl. .................................... 47/1.4; 210/15
[51] Int. Cl.² ...................... A01G 7/00; C02C 1/02
[58] Field of Search ............. 47/1.2, 1.4, 58; 210/3, 210/4, 7, 8, 13–15

[56] References Cited
UNITED STATES PATENTS

| | | | |
|---|---|---|---|
| 2,867,945 | 1/1959 | Gotaas et al. | 47/1.4 |
| 3,243,918 | 4/1966 | Machiedo | 47/1.4 |
| 3,385,786 | 5/1968 | Klock | 47/1.4 |
| 3,420,739 | 1/1969 | Bongers et al. | 47/1.4 X |
| 3,431,200 | 3/1969 | Davis et al. | 210/10 |
| 3,521,400 | 7/1970 | Ort | 47/1.4 |
| 3,645,040 | 2/1972 | Ort | 47/1.4 |
| 3,768,200 | 10/1973 | Klock | 47/1.4 |

Primary Examiner—Robert E. Bagwill
Attorney, Agent, or Firm—Owen, Wickersham & Erickson

[57] ABSTRACT

A method of producing an algae product and of purifying aqueous organic waste material to provide clean water. Starting algae and aqueous waste are admixed in sufficient amount to provide nutrients for the algae, which are grown in symbiotic relationship with aerobic bacteria present. The mixture is aerated and, if desired, carbon dioxide added, and is exposed to alternate periods of light (e.g., 1/2 second to ten seconds) and darkness (about ten times as long as the light period) to accelerate growth of the algae, harvesting the algae product to maintain the growth rate at a very high level. A device for effecting agitation and intermittent light exposure includes a reaction tank having a generally vertical wall in the form of a parabolic curve, injectors debouching into the bottom of the tank opposite the parabolic-curve wall and causing circulation so that injected and other material is forced rapidly upwardly, and a baffle transversely across the upper portion of the tank. The baffle supports and directs the flow of a selected proportion of an aqueous reaction mass across the upper portion of the tank, exposing the selected proportion to limited exposure to a source of light. A system for carrying out the method is provided.

40 Claims, 4 Drawing Figures

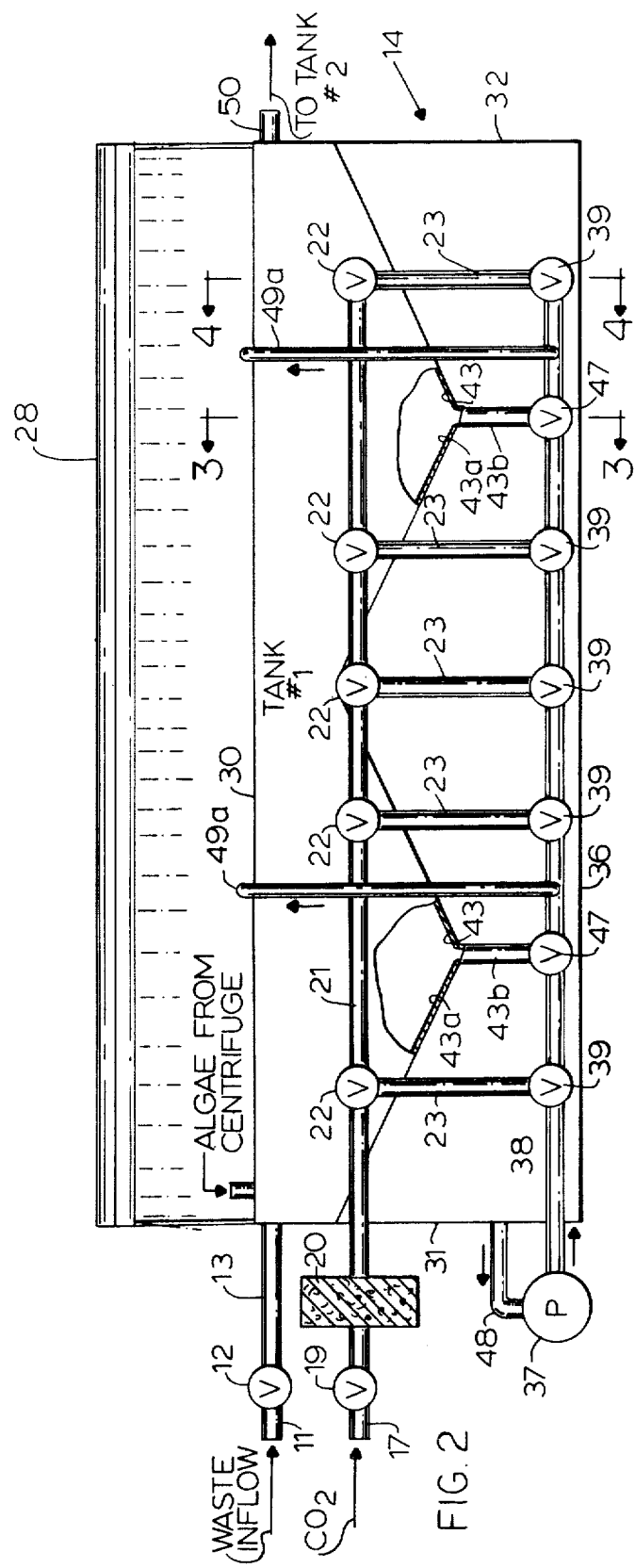

# 3,955,318

WASTE PURIFICATION SYSTEM

CROSS REFERENCE TO RELATED APPLICATIONS

This is a continuation of application Ser. No. 342,516, filed Mar. 19, 1973, which was a continuation-in-part of application Ser. No. 205,152, filed Dec. 6, 1971, both abandoned.

BACKGROUND OF THE INVENTION

This invention concerns a method of pollution control obtained by growing unicellular and similar algae with the aid of an organic waste nutrient medium, including a phosphorus-providing substance and nitrogen-providing material. In another manner of expression, the invention concerns a method of pollution control wherein unicellular and similar algae, such algae being a good source of protein, are grown in symbiotic relationship with aerobic bacteria on nitrogen-providing or protein-providing aqueous waste materials such as portions of sewage, cannery wastes, etc., in a way that produces purified water, an algal mass high in protein, and free oxygen, which is liberated to the atmosphere. In another aspect, the invention relates to an apparatus especially suitable for admixing algae and nutrient waste material and exposing portions of the admixture to intermittent light exposure and darkness of desired time length.

Pollution control is one of the most important factors in preserving a balanced environment. There are many methods of removing pollution from municipal wastes, ranging from simple municipal primary treatment, to complex biological and chemical primary or secondary or tertiary treatment, such as the Tahoe Public Utilities Department experimental plant, for instance. All these systems are primarily concentrated on removal of biological oxygen demand (BOD) wastes. BOD wastes are those wastes which require oxygen and take it from the water.

Any attempt to purify waste water cannot fail to help the environment, but this simple prior-art removal of pollutants cannot be considered as efficient in a balanced ecological system. In fact, the disposal of certain wastes in streams and lakes can have a beneficial effect. In some cases, thermal pollution has had a favorable effect on trout population. However, most wastes introduced into the environment have a deleterious effect on the water. It is essential to ascertain the total ecological impact of water treatment. Ideally, the object of any pollution treatment should be to return the wastes to the environment in the least harmful way, while extracting or converting as much waste as possible to usable form.

It is among the objects of this invention to provide a balanced treatment of waste, not only to provide pure water, but to use waste as a resource to produce a source of protein. A further object of the invention is to produce oxygen and to liberate it into the atmosphere in substantial quantities. Still further objects are to enable the treatment of wastes to be carried on with minimized costs in material, equipment, operation and recovery. It is a specific object to produce, from aqueous wastes, purified water which can be used for domestic purposes (after chlorination), industrial cooling, irrigation or as return to ground water or for all such purposes.

SUMMARY OF THE INVENTION

This invention concerns a method for growing unicellular and similar algae and for purifying polluted water. It uses as nutrient media nitrogen-providing aqueous wastes, such as cannery or other food-processing wastes, sewage, or the like, especially when these have been comminuted and the bulk of the solids removed and fed to well-known digesters. More particuarly, it concerns a method wherein a mixture of algae and waste is exposed to light in a particular manner to maintain exceptionally good growth rates of the algae. An apparatus and a system for effecting such results are also provided.

In one manner of expression, this invention provides a method of growing single-celled protein (SCP) from waste. By growing unicellular or similar algae under controlled conditions, a biomass of cells is sustained at a logarithmic growth rate in a self-regulating continuous culture. Under these conditions, the algae consume a very high percentage of the wastes in the water, synthesizing protein in the biomass and purifying the water.

In the method of this invention, unicellular or similar algae are admixed with a nutrient waste material which provides nitrogen and phosphorus to foster growth of the algae in an aqueous medium, to form a growth zone or biomass. The biomass includes aerobic bacteria, which are grown in symbiotic relationship to the algae. Sufficient waste is admixed with the algae to support rapid growth of the algae under the influence of controlled light. The biomass is subjected to controlled action of light to effect the rapid growth of the algae and the consumption of the waste. An algae product is withdrawn, and purified water is separately recovered. In a particularly advantageous procedure, the admixture is subjected to light intermittently, that is, to alternating periods of light exposure and darkness of certain durations. The reacting mass is continuously agitated and recirculated, suitably by injection of air, and carbon dioxide is also advantageously introduced into the biomass to stimulate growth of the algae.

GENERAL PRINCIPLES AND FORMULAE OF THE INVENTION

The waste employed can be sewage or cannery waste or other food-processing waste. However, domestic sewage is particularly useful because it provides nitrogen and phosphorus, the latter being derived in many instances from the detergents present therein, as well as trace elements, such as calcium and magnesium that are usually present in natural tap water. However, other nitrogenous or proteinaceous wastes can be employed, and the invention also contemplates the incorporation of supplemental amounts of nitrogen, phosphorus, and potassium if the waste itself does not contain sufficient of each to sustain the desired growth rate of the algae. In this event phosphorus can be added as a water-soluble compound, e.g., a metal salt of a phosphoric acid such as a water-soluble orthophosphate of an alkali metal or ammonium, especially potassium hydrogen phosphate. Phosphate fertilizer in liquid form is also useful. The nitrogen can be added as a solid nitrogenous compound, suitably as urea or a protein.

The algae useful herein are microscopic algae, such as exist in single cells or small groups of cells and are also termed herein "unicellular algae". The filament-form microscopic algae are also useful but are less advantageous than the single-cell or unicellular algae, being limited as to growth rate by the breaking of the filaments. The unicellular algae useful herein include Chlorophyta, Euglenophyta, Christophyta, Pyrrophyta, Cyanophyta and Rhodophyta. The useful algae exhibit a rapid growth rate, tolerance of wide substrate concentration range and tolerance of or resistance to high temperatures up to about 35° C. One strain of Chlorophyta algae which has been found particularly advantageous to use is Chlorella sp., particularly a strain which has developed after 3 weeks' operation of the process described herein. Other particularly advantageous strains of Chlorophyta algae are Chlorella TX115, which is a thermophilic strain of algae, *Chlorella pyrenoidosa* and *Scenedasmus obliquus*. Chlorophyta are advantageous in general because of fast growth rate and hardiness of groups of cells. Some algae, however, can be grown for a specific by-product. For instance, *Porphyridium cruentum* (a Rhodophyta) can be grown as a source of carotene-bearing algae; this is one of the few microscopic forms of red algae suitable for the system of this invention.

Aerobic bacteria exist naturally in the system. They are present in the air and water but come mainly from the waste. They consume carbon and carbonaceous material in the waste, using oxygen to produce carbon dioxide, which they liberate. This carbon dioxide helps the growth of the algae, and the oxygen liberated by the algae helps the growth of the aerobic bacteria. Hence, there is a close symbiotic relationship in this method between these aerobic bacteria and the algae. The algae consume the salts, the phosphates, the calcium, magnesium, and iron ions and such other materials, with the aid of the carbon dioxide from the bacteria, while the bacteria act mainly on the molecules or ions containing carbon.

As will be seen, gas is injected in order to provide circulation of the liquid suspension. The more oxygen present in the injected gas, the greater tendency there is for the aerobic bacteria present to predominate; conversely, the more carbon dioxide present in the injected gas, the greater the tendency for the algae to predominate. The mixture of oxygen (air) and carbon dioxide can therefore be used to provide a desired ratio of algae to bacteria, and this invention does this. In addition, the oxidation helps to convert some of the waste by simple oxidation. It has been found that a ratio of oxygen to carbon dioxide of about five or six to one achieves a very satisfactory balance of algae to bacteria. Thus, in one instance, the injection of 80 cubic feet per minute of air along with 3 cubic feet of carbon dioxide worked very satisfactorily in a system having an 800 gallon liquid capacity. This meant that the bacteria weighed about 5% as much as the algae in the system at all stages of growth. This injection of gas into the biomass also provides agitation of the mass and aids growth of the algae and decomposition and utilization of the waste materials. For at least some of the algae carbonates or combustion gases can be used as a source of the carbon dioxide. The Institut Francais du Petrol has reported the growth of Spirulina maxima in a bicarbonate medium.

The mass is subjected to the action of light, which can be daylight or aritifical light of similar wavelength. The light source selected is of such intensity as visibly to promote growth of algae, while avoiding bleaching them substantially. In a particularly advantageous method of working, the mass is subjected to intermittent periods of light, that is, to alternate periods of light and darkness. In one mode of operation, for instance, the growth rate of the algae cells can be increased by a factor of seven by subjecting the algae to a short period of high intensity light, up to about 8000 foot candles, followed by a dark period about ten times as long as the initial light period. The intensity of the light source used can be from 400 to 8000 foot candles, in order to obtain excellent results by this invention. It is necessary to subject the algae to at least 400 foot candles to trigger photosynthesis. The artificial light used may be of about the same wave length as that of natural daylight, or an artifical light emitting at 440 and 680 nanometers may be used with excellent results.

The alternation of light with darkness is best thought of as a modification of the diurnal cycle, and the exposure to light should not be too short. It has been found that the cycling reaches its peak efficiency where the light exposure lies in the range of 0.9 seconds to 1.2 seconds at sufficient light intensity to saturate the culture for photosynthesis. The light intensity acting on the algae depends, of course, on the depth and light intensity of the culture. Below about 0.9 seconds, the efficiency of the system decays, because the power required to establish the flow giving the correct cycling becomes excessive and uneconomical. It will be recalled that the period of darkness is preferably about ten times as long as the period of light, and a mechanical limit of practicability appears to be reached at about one-half second of light exposure. Shorter times require too high a stream velocity where the stream is exposed to the light; times shorter than one-half second of light exposure tend to be less efficient biologically also, though the system still functions, to a lesser extent. Times longer than 1.2 seconds are less efficient, though still workable, and a practical maximum is about 2 seconds. As light exposure gets longer and longer the result approaches nearer and nearer to what one gets from nature—where the process is about one-seventh as efficient as it is with exposures to light in the present invention of about 1 second, followed by about 10 seconds of darkness.

This system is best obtained by mechanical circulation rather than by turning lights on and off, for a proper mechanical circulation system enables the light to be on all the time and the handling of a much greater volume of sewage or other waste in the same size of system.

As indicated above, the mechanical circulation can be obtained by a series of gas injectors in combination with a suitably designed tank, to circulate the liquid mixture or suspension around, over, and beneath a light barrier or baffle. This use of gas injectors to accomplish the circulation has the advantage that the gas can be a mixture of air and carbon dioxide that maintains a desired ratio of algae to bacteria in the system, thus accomplishing two desirable results with a single mechanism.

The speeding up of the diurnal cycle in the present invention should not be confused with the use of flashing light in very brief light exposures, such as a few milliseconds. There is considerable argument as to the actual process of photosynthesis, but it is generally agreed that a photon striking the thylakoid (photoreceptor) of the cell causes the thylakoid to lose an electron, which triggers a series of chemical reactions eventually producing the end products of photosynthesis.

As the initial electron transfer is caused by photons freeing electrons from the thylakoid, the thylakoid is gradually oxidized, thus reducing the photosynthetic efficiency of the cell. In nature, the cells are triggered only during sunlight and the cells regenerate during the dark. During the early morning hours, the rate of inorganic uptake and photosynthesis in the cells is at its highest rate. The phenomenon is probably caused by the healthy condition of the thylakoids and the availability of $CO_2$ from bacterial activity which has continued during the night. The higher levels of inorganic carbon are apparent by the lower pH of a natural algae culture in the morning hours before sunrise.

As the sun travels overhead, more light in the far red spectrum is able to penetrate the culture (far red light is absorbed in water to a much greater extent than wavelengths associated with photosynthesis). The far red light causes a rearrangement in the chlorophyll molecules, producing a quenching effect on the 680nm light uptake in the cells, altering the characteristics of the thylakoids.

It may be that the far red (700 + nm) quenching effect contributes to the overall ageing of the typical culture, causing variations in the lipid-to-protein ratio of the cell and has a progressive and cumulative effect on the oxidation of the thylakoids.

In the system of the present invention, the algae is subjected to light for a short 0.5 to 2-second period to take advantage of the high rate of photosynthesis following a dark period, with minimum oxidation of the thylakoids, and then is subject to a dark period sufficient to allow the regeneration of the cell. This dark period is about ten times as long as the light periods. More broadly, the algae is stimulated for a sufficient period to take advantage of the initial high rate of activity, and is then subjected to sufficient dark to regenerate the cell.

During the lighting cycles, the bacteria constantly oxidize organics to provide sufficient $CO_2$ to provide an inorganic carbon source for the algae. In prior-art systems, sewage is sometimes fed through a separate bacterial process before the photosynthetic process, but the present invention establishes a symbiotic, simultaneous relationship between the bacterial and algae cultures to simultaneously reduce the pollutants in the sewage. At the same time, $CO_2$ is added as a gas to insure that the algae predominate, as they then do not have to rely on bacterial activity for inorganic carbon.

According to this invention there is now provided a method, device, and system whereby the desired rapid growth rate of algae in the mixtures described herein is attained, and the biomass as described is injected with air and, if desired, $CO_2$ gas, and exposed to alternate periods of light and darkness to obtain an algae product and purified water, using the wastes as described as a starting material or nutrient for the algae. The method can be carried out batchwise but is more readily controlled and more economical when carried out continuously.

Largely, waste is judged by its nuisance value, odor, solids content, and appearance. A good general yardstick is the well-known biological oxygen demand test, i.e., determination of the amount of oxygen required to stabilize organic matter in waste under standardized conditions. The usual measure of waste treatment plants is "5 day BOD", or how much of the BOD substances that require 5 days to stabilize are removed upon standing with access to light and oxygen.

The present invention, however, concerns utilization of the waste as nutrient for algae and the symbiotically grown bacteria. To grow one gram of algae requires approximately 0.4 gram of carbon, 0.1 gram of nitrogen, 0.01 gram of phosphorus, and some trace elements that are normally present in the water. Domestic sewage is, therefore, a remarkably balanced diet for the algae.

The algae convert 97-99% of the convertible elements of the waste. However, the amount of algae grown is not directly comparable to the waste content of the water because, in breaking down the waste, the algae liberate substantial quantities of oxygen. In practice, about 65% of the waste is normally converted into algae as the biomass grows, and the rest is given off as free oxygen, since the alga is a photosynthetic organism. It should be noted that these figures are approximate, for the rate of growth of the algae varies with the conditions of culture. However, the final amounts of waste removal are definitely established, and waste removal to a given level is a function of time. Considering the sewage input of the average person, it is possible to produce 0.11 lbs. of algae per person per day. Therefore, to convert the total waste input in a treatment system, the invention cultures a biomass of cells at least about equal in weight to the waste that is to be converted.

The density of domestic waste is diluted by water from household use, and thus the total convertible sewage input is from 1 to 2 grams per liter, so that an equivalent cell density should be maintained in the system where the algae grow, where it is desired to double their mass in a 24-hour period. The initial mass of cells is selected to be large enough to increase in size equal to the sewage input.

Therefore, where a higher cell density is maintained, the supply of waste is increased to supply the nutrients for the algae. Also, if the growth rate is increased, more nutrients are provided. In one procedure, this can be done by increasing the flow-through rate of the waste, bringing more nutrients into contact with the biomass in a given period of time. Cell density is the packed volume or weight of cells per liter of culture. The lower limits are governed by what is needed to avoid excessively slow flow-through rates, while the upper limit, which is about 150 grams per liter, is governed by light absorption. A density of 10 grams per liter comprises a dry solids content of about 10%.

The amount of algae in the system must be such, that at a given growth rate for the algae, it will increase in mass proportionate to the waste loading on the system. In other words, the algae's mass must increase proportionally to the loading, assuming corrections for heat loss and gas evolution in the growth of the algae.

The purpose of the system's continued cycling is to maintain a high rate of growth. As the residence time of the system is designed to accommodate a certain waste loading per unit time (1.5–2 hours in one installation, the algae will be cycled from light to dark several hundred times in this interval.

The principal theoretical factors can be formulated in a theoretical equation, which is completely valid only if one hundred percent efficiency is obtained in all aspects of the system. Of course, there will never be such one hundred percent efficiency. Some of the algae will cling to the tank walls and not circulate, and this affects efficiency. Some of the algae are damaged in the centrifuge before they are recirculated. The response time to changes made by the control system, to change densities of algae in response to changes in loading, is not instantaneous but a finite time. Moreover, it is apparent that not all of the algae can be brought into contact on an instantaneous basis with the pollutants that have to be broken down. However, the equation is helpful, if an adequate margin of safety is provided.

Without correcting for the respiration rate of the algae, which is a negligible factor, this theoretical relationship can be formulated as follows:

$$V = I \times \frac{W}{C} \times \frac{T}{24}$$

Where:
V = culture volume
I = total sewage inflow
W = waste content of sewage in grams per liter
C = algae content of culture in grams per liter
T = doubling time of biomass For instance, the best results obtained in laboratory studies give a cell density value of 40 grams algae per liter with a doubling time of 3.6 hours, where the convertible sewage input is 2 grams per liter.

According to data of the American Public Health Association, the average BOD production per person per day is 0.17 pounds. In any system of waste control, man must be considered as part of the system, and the typical human input is as follows:

ANALYSIS OF HUMAN WASTE

| Substance | Amount |
|---|---|
| Solids | 0.22 lbs/day |
| Urine | 3.30 lbs/day |
| Fecal $H_2O$ | 0.33 lbs/day |
| $CO_2$ | 2.25 lbs/day |

The first three items of the above analysis are the contents of the sewage which are of prime concern in sewage treatment, but the carbon dioxide is included too, for it helps demonstrate the ecological efficiency of the SCP waste control. As mentioned, it is necessary to remove the BOD substances, a large percentage of the waste being water or dead cellular material. Therefore, the solids content is approximately 0.17 lbs per person per day.

Applying the above to a city of 10,000 people, the following figures are obtained:

Total volume of waste per day
 (population × 50 gal. per day) = 500,000 gals/day
Usable content of sewage
 (population × .17) = 1700 lbs/day
Algae production
 (usable content of sewage
 convertible into algae) = 1100 lbs/day Thus, from the above formula, the sewage of a city of 10,000 people would be treated with a culture volume of:

$$V = 500,000 \times \frac{2\ g/l}{40\ g/l} \times \frac{3.6}{24} = 375\ gal. = 1634.4\ liters.$$

As another example, a city producing one million gallons of sewage per day would need approximately fifty units of this invention in order to provide an adequate safety margin for rain overload and for fluctuations in the feed rate of the sewage.

The modes of carrying out the treatment involved in the above formula will be explained below.

A culture of cells exists in three basic stages: a lag phase, a logarithmic growth phase, and a rest phase. When nutrients are made available to the algae culture, the growth rate does not change instantly, but continues at, or slightly above, its previous level. After the biomass responds to the influx of nutrients, the cells then enter a logarithmic growth phase. If allowed to continue indefinitely, the cells will consume the nutrients and enter a rest phase.

In one manner of procedure, a culture grown on sewage can be maintained at the highest portion of the logarithmic growth phase. By harvesting the algae, such growth can be maintained at such high level. However, if the biomass is allowed to exceed such growth phase, it will enter the rest phase and become dormant. It is then necessary for the culture to go through the whole cycle to restore the desired growth rate. Therefore, it is advantageous to maintain the culture somewhat below optimum levels. Closer control of the culture is desirably effected as optimum values of growth are approached, as by regulating the flow-through rate of the system or the portion of the harvested algae that is recycled.

The pH of the biomass is maintained at about neutrality and if it increases substantially above neutrality the algae can be harvested to reduce to the preferred value. If the pH falls substantially below neutrality, a buffer such as urea can be added. The invention is operative over a wide pH range, as low as 3.5 and as high as 11, though a pH of 6.9 at the input is typical, and a pH of 7.1 then results in the purified effluent.

The algae utilize and consume the convertible components of the waste material by photosynthesis, and at the same time are subject to bleaching or destruction by excessive exposure to light. Thus, the algae are advantageously protected from substantial bleaching in the present process, while being provided with adequate light to effect the photosynthesis, by providing alternate light and dark periods, by maintaining a suitable depth of biomass exposed to light, and, especially in a continuous process of exposing a turbulent flowing stream of the biomass to the light whereby no static top layer is overexposed. The optimum depth of algae cultures exposed to direct sunlight of about 8000 foot candles is about 2.7 inches at a culture density of 150 gms. per liter. The culture follows the Beer-Lambert law of light absorption, by which the light absorbed by the particles in solution is directly proportional to the density of particles in solution, and the preferred depth can be easily calculated for a given density of single-celled algae. The culture can be controlled in all cases by the use of a total oxygen demand apparatus (TOD). This can be used to compare the TOD of the influent and the effluent to check on the reduction of TOD. In other words, the TOD loading on the system is a function of the flow rate and pollutant density. Thus, the removal of TOD substances can be regulated by the flow rate in the system; high initial TOD reducing the flow, and low TOD increasing it. The effluent TOD is monitered to assure the quality of the effluent, which will also regulate the inflow if tolerances are exceeded. This system is the most sensitive, but is expensive.

BRIEF DESCRIPTION OF THE DRAWINGS

The invention and some modes of carrying it out will be illustrated by the more detailed description below and by the annexed drawings wherein:

FIG. 2 is a view in side elevation of a tank and associated elements suitable for carrying out the process of this invention;

DESCRIPTION OF THE PREFERRED EMBODIMENT

Figure 1:
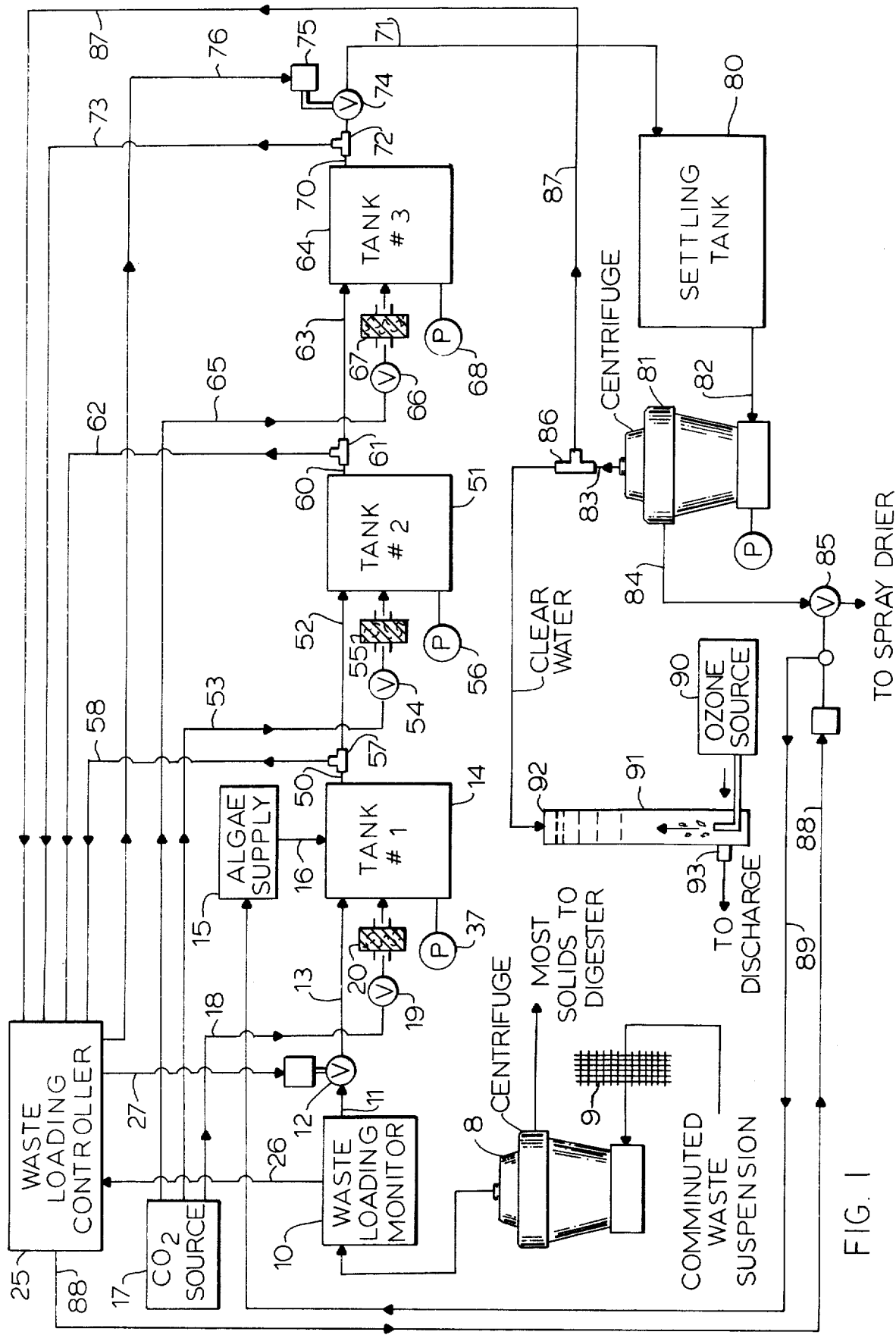
FIG. 1 is a flowsheet showing one embodiment of the procedure according to this invention.
Figure 4:
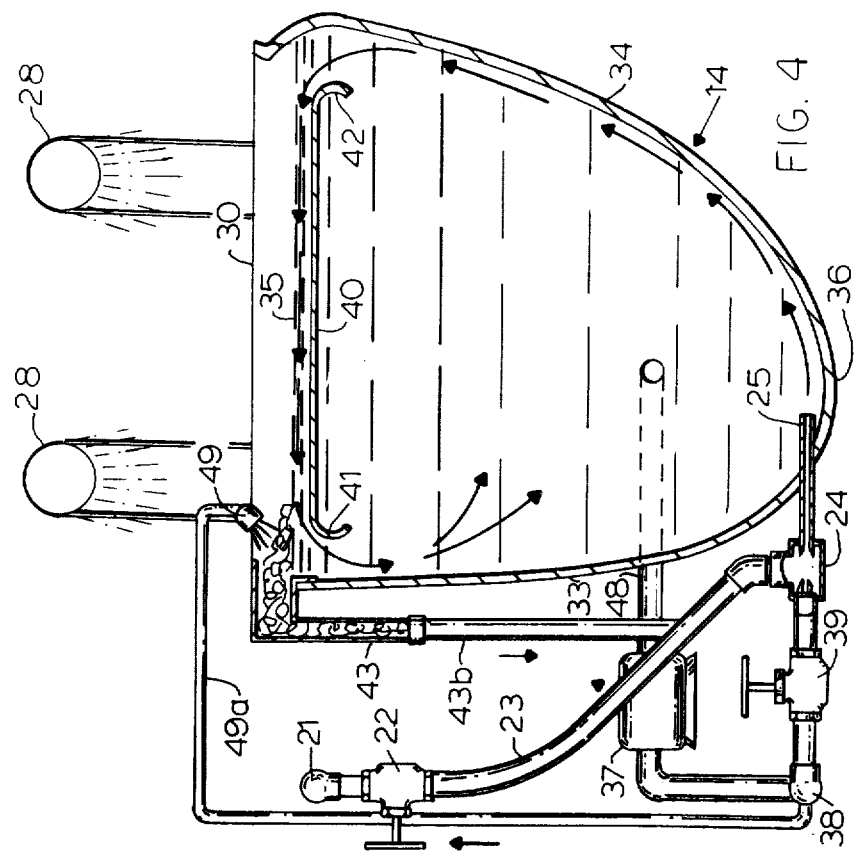
FIG. 4 is a vertical cross-sectional view taken on line 4—4 of FIG. 3.
Figure 3:
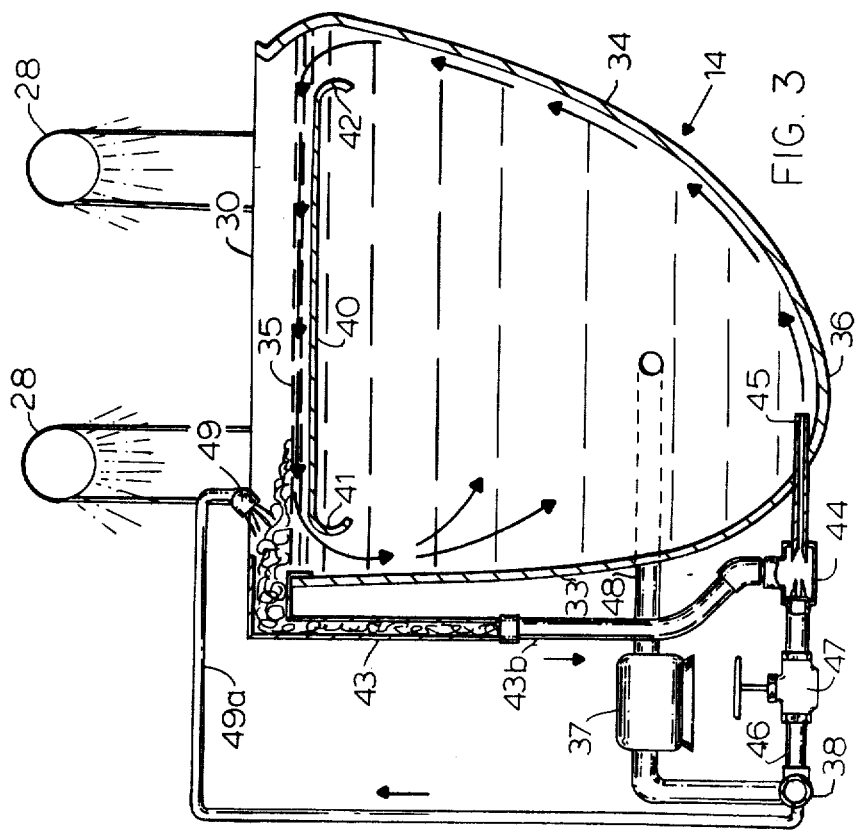
FIG. 3 is a vertical cross-sectional view taken on the line 3—3 of FIG. 2.

One mode of continuously carrying out the invention will be described with reference to FIGS. 1-4. Aqueous domestic sewage is preferably treated, as is normal, by comminuting it. Then the large particles and non-degradable materials may be removed. For example, a centrifuge 8 may be used, the centrifuge being provided with a protecting screen 9. About 90% of the solids may be removed by the centrifuge 8 and sent to conventional digester, which is already present in most sewage treatment plants. Thereby, the turbidity of the incoming sewage is reduced by about 90%, so that the ability of the light to reach the algae is enhanced. The sewage may be pretreated by settling, if desired. Another alternative is to send the sewage through a strainer; a micron strainer may be used to filter the sewage through a 15-micron mesh screen. This and settling are usually less efficient than centrifuging, but like the centrifuge 8 would be placed ahead of a waste-loading monitor 10.

The screened or centrifuged sewage is passed through a waste-loading monitor 10 and is fed by a conduit 11 through an input and flow-control valve 12 and a conduit 13 into a tank 14. A supply 15 of algae also feeds algae to the tank 14 by a conduit 16, to initiate the reaction, aerobic bacteria being inevitably present already. Initially, the algae may be supplied to all tanks 14, 51, and 64, but thereafter supply to the tank 14 alone is required. The tank 14 is exposed to the atmosphere, and, if desired, a source 17 of carbon dioxide supplies the tank 14 with that gas, mixed with air if desired, and introduces it into the mass in the tank 14 through a conduit 18, a valve 19, a filter 20, and a manifold 21 (see FIG. 2) having a plurality of valves 22, pipes 23, and injectors 24 (see FIG. 4). Ambient temperatures are usually satisfactory, since sewage is normally between 40° and 80°F. anyway, and this is the best temperature range.

The valves 12 and 19, as well as the valve 85 in the recycling conduits for algae product as later described, can be manually operated, but advantageously they are connected to and electrically controlled by a waste loading controller 25 (to determine the rate of feed by the amount of nutrients in the feed and by the efficiency of the process as measured by the qualities of its output), using commercially available and conventional devices. The waste loading controller 25 also controls the waste loading monitor 10 by a line 26 to monitor the inflow, and it controls the valve 12 by a line 27. As will be seen, the controller 25 may be influenced by the density of algae in the outflow from each of the reaction tanks and some chosen quality of the clear water exiting from the centrifuge 81, later described. The chosen quality may be turbidity, biological oxygen demand, or the phosphate content, nitrate content, sulfate content, or dissolved oxygen content. More than one such quality may be used.

In a normal sewage application of the invention, the phosphate content may be taken as the growth-limiting factor, or the content of some other nutrient may be used. The recycle rate of the algae may be controlled so that the monitored nutrient is never reduced below a certain level and so that it never exceeds a certain level for long. A lowering of the phosphate (or other growth-limiting nutrient) will not produce any radical change in growth rate until the point is reached at which the algae starts to slow down and go into an endogenous respiration state. A typical control cycle is described later.

The waste loading controller 25 is an electrical device receiving signals from various monitors and using these, through standard controls, to actuate controls. Thus, monitoring stations 57, 61, and 72 may each read the phosphate content or other nutrient content in the liquid there and send an electrical signal corresponding to that content to the waste loading controller 25. Limit switches or other device may be preset to react to open or close at desired amounts. At the appropriate limits the waste loading monitor 10 may signal the optical density to the controller 25. The controller 25 then acts on solenoid valves 12 and 85 to change the rate of admission of waste to the system and the amount of algae recycled thereto. The system is of a type well known, using known devices to read phosphate or other content and to cause appropriate action thereby, as set by an operator.

The tank 14 (see FIGS. 2 to 4) is open at its top 30, so that the algae layer is exposed to a light source, suitably daylight. However, 24-hour operation and operation on dark days may be assured by lamps 28, preferably comprising fluorescent tubes of about 200 watts emitting light at 440–680 nanometers. The lamps 28 may be supported about eight inches above the liquid in the tank 14. The lamps 28 may have their upper surface reflectorized to direct all light down into the tank 14. The lamps 28 are preferably oriented horizontally along the length of the tank, parallel to the surface of the water to be exposed to their light. The tank 14 has end wall 31 and 32 which may be planar, a nearly vertical front wall 33 and a rear wall 34 in the form of a generally parabolic curve to help provide the desired circulation of a biomass 35 in the tank 14. The tank 14 may be made from molded plastic or from stainless steel, or from concrete coated or covered with a suitable plastic, such as polypropylene. At the base 36 of the tank 14 (see FIG. 4) is a series of the injectors 24, having an outlet 28, each being connected to the manifold 21 by a pipe 23. Each injector 24 is also connected to a pump 37 (FIGS. 1 and 2) by a second manifold 38 and a control valve 39 at each injector 24. Advantageously, the injectors 24 are horizontally disposed across a portion of the base 36 of the tank 14. The combination of the parabolic configuration of the back wall 34 with the injectors 24 has been found to provide suitable agitation and circulation and the proper flow rate of the biomass 35 to obtain the desired periods of exposure of the biomass to light and darkness, alternately. Thus, the fluid-gas stream from the injectors 24 cause a portion of the culture to flow up the wall of the tank, following the parabolic arc and establishing a lenticular flow, thereby causing the flowing stream to traverse a horizontal baffle 40 disposed in the upper portion of the tank 14, thereby exposing the culture to light for about one second.

The horizontal baffle 40 (FIGS. 3 and 4) is suitably supported, e.g., by bolting it at each end to the end walls 31 and 32. The baffle 40 is spaced from the front and rear walls 33 and 34 and is preferably curved downwardly at its transverse sides 41 and 42 to promote the flow of the circulating mass. The baffle 40 is located high enough so that the light that penetrates to it through the mass 35 is at an intensity of at least 400 foot candles, and typically about nine-tenths of the biomass 35 in the tank lies below the baffle 40. The width of the tank 14 (between the walls 33 and 34 at the upper end 30) is governed by the amount of time for which the algae is to be exposed to the light as it flows over the baffle 40, and thus depends partly on the flow rate thre, peferably about one second. The interior surfaces of the tank walls 31, 32, 33, and 34 and the lower or interior surface of the baffle 40 are advantageously painted black, and the upper surface of the baffle 40 is preferably light-reflective, to ensure or enhance the dark-light relationship.

A plurality of foam-offtake conduits 43 is disposed at the front wall 33 of the tank 14 above the baffle 40 at the level of the desired top surface of the biomass 35 flowing over the baffle 40, to skim off foam which may form thereon. The conduits 43 have a broad V-shaped upper portion 43a leading into pipes 43b at the lower end, which connect there to associated injectors 44 (FIG. 3) having injector outlets 45. The injectors 44 create a vacuum force in the conduits 43, causing the foam to break up; they are also connected to the pump 37 by conduits 46 and are individually controlled by valves 47. The injectors 44 recycle the foam to the tank 14. The intake side of the pump 37 is connected to the tank 14 by a pipe 48, so that the pump 37 recycles a portion of the circulating mass 35 from the tank 14 through the various injectors 24 and 44 back into the tank 14. With some waste, it is advantageous to include a series of foam breakup nozzles 49 connected by a pipe 49a to the manifold 38; the nozzle is directed against the foam from above and is directed toward the foam-offtake pipe 43.

In this embodiment, the tank 14 is provided with an outlet pipe 50 (FIG. 1) at the upper or top portion of the end wall 32 to conduct treated material to a second tank 51, via a conduit 52. Carbon dioxide from the source 17 may also be supplied to the tank 51 by a conduit 53, valve 54, filter 55 and a manifold system of injectors, etc., substantially identical to that for the tank 14. The tank 51 may be identical in shape and in general operation to the tank 14 and may be equipped with a pump 56 like the pump 37. Control of inflow to the tank 14 may be influenced by signals from an outlet monitor station 57 and a signal line 58 acting on the waste loading controller 25. Similarly, the outlet 60 from the tank 51 may be provided with an outlet monitor station 61 connected to the waste loading controller 25 by a signal line 62.

The outlet 60 leads via a conduit 63 to a third tank 64, which may be substantially identical to the tank 14. It may be supplied with carbon dioxide from the source 17 via a conduit 65, valve 66, and filter 67, etc., and it may have a pump 68. The third tank 64 may have an outlet 70 leading into a conduit 71, and a monitoring station 72 may send a signal by a line 73 to the waste loading controller 25. A valve 74 in the conduit 71 is controlled by a solenoid or other device 75 actuated by the waste loadng controller 25 through a signal line 76. The conduit 71 leads thence to a settling tank 80.

The settled mass from the settling tank 80 is conducted to a centrifuge 81 by a conduit 82, and clear water is withdrawn from the top of the centrifuge 81 through a conduit 83. A concentrated algae product is withdrawn from the centrifuge 81 through a conduit 84 controlled by a valve 85 and sent to a spray drier (not shown). A monitor station 86 in the clear water conduit 83 sends signals to the waste loading controller 25 via a signal line 87, and the valve 85 also sends signals to the waste loading controller 25 through a line 88. Some or all of the algae product can be diverted through a pipe 89 and recycled to the tank 14 and utilized as the algae input thereto, after operations have gotten under way. In good constant conditions, only about one-fourth of the algae need be recycled, sometimes less. In cases of varying load, however, where large increases in load come suddenly, up to 95% of the algae may have to be recycled for awhile. The control system of the invetion is able to accommodate these changes.

Clear water from the centrifuge 81 can be used for any desired purpose and if for potable use, may be suitably chlorinated. It is advantageous to use an ozone disinfection process, this being particularly effective because of the high qualtiy of the water discharged from the algae system. Because of this, only a small dosage of ozone is required to eliminate essentially all of the virus and bacteria in the effluent. A commercial ozone generator 90 may be used to produce ozone gas which is then bubbled through the effluent, ideally in a vertical column 91 with a downward flow of liquid, which enters at the upper end 92, and an upward flow of gas. The clear effluent, ozone purified and therefore bacteria free, exits at the outlet 93.

The device is useful for continuous culture, a process wherein the microorganisms are maintained at a fixed rate of nutrient uptake and cell division, all factors affecting culture being maintained as nearly statically as possible. Continuous cultures differ from random aged cultures in which the cells may exist in a variety of phases of growth.

In an example of a continuous method of making purified water and a high protein algae product according to this invention, screened aqueous domestic sewage is comminuted to pass through a 60-mesh screen and is fed through the waste loading monitor 10 into the tank 14 in the device and system described above at a rate of 14 gallons per minute for tanks of a valence of 150 gallons each. A supply of Chlorella sp. is also placed in the tank, in the ratio of about 40 gms. per liter of the algae per 2 gms. per liter of convertible components of the sewage. The waste loading controller 25 may be replaced by hourly analysis of samples at the monitoring stations. For example, pH alone may be used, with an input at 11 of pH 6.7, and readings at stations 57, 61, and 72 of 6.8–6.9, 7.0, and 7.0–7.1, respectively.

In the operation of the tank 14, the sewage containing the algae is circulated in the tank 14 by passing it through the pipe 43 and pump 37 and through the series of injectors 24 and 44 that are placed horizontally along the bottom of the tank 14. The injectors 24 and 44 draw in air, or $CO_2$ if a carbon source is required by the algae, through the filter 20, and the air/water mix is injected across the tank 14. The mixing of air under pressure in the pump and injectors aids in the oxidation of the medium, breaking down the domestic waste into forms readily available to the algae.

The curve of the tank wall 34 opposite the injectors 24 and 44 is a partial parabola to insure that the air/water mix from the injectors 24 and 44 follows the wall 34 of the tank, rather than bubbling up into the mass in the tank 14. The tendency of a stream of liquid to follow a surface, or lenticular flow, is important in establishing a rotational effect in the tank. The air in the stream lifts the water up the opposite wall 34 of the tank 14, where it is spilled across the baffle 40 and exposed to sunlight of about 8000 foot candles intensity for about 0.9 to 1.2 seconds, preferably, in order to prevent retarding the growth rate of the algae, while giving it enough light to grow well. The culture medium 35 then traverses the baffle 40 and flows down the front wall 33 of the tank, and, being highly aerated, settles slowly and turbulently, mixing with the remainder of the culture, and then repeats the cycle. In actual operation, the flow is almost entirely random, thus ensuring that the culture is exposed to light at the correct ratio, as about one-tenth of the culture is above the baffle 40 at any given time, making a dark-to-light exposure ratio of about 10:1. Foam forms at the upper surface of the biomass 35 flowing across the baffle 40 and is drawn off at the conduits 43, and is broken up and returned to the mass in the tank 14 by the injectors 44, which are disposed in the bottom of the tank 14, suitably in the same manner as the injectors 24. The pump 37 forces air, $CO_2$ (if used), recycled medium, and incoming sewage through the injectors 44. The injectors 24 and 44 are preferably disposed generally perpendicularly to the surface of the wall 34. The use of a rubber stator pump as the pump 37 has been found to substantially eliminate rotifers which feed on algae and may invade the system.

The depth of the baffle 40 below the top of the biomass 35 is governed by the light penetration at the density at which the culture is maintained. In one embodiment the depth was 2.7 inches, in direct sunlight, at a culture or biomass density of about 140 grams per liter. It was determined that the biomass cells of the type employed here could tolerate direct sunlight for approximately one second in turbulent culture, and the flow rate was adjusted to provide such rate of flow across the baffle 40. The volume of the tank 14 below the baffle 40 is ten times the volume of culture exposed to light above the baffle 40, for best results. This ratio can vary, however, and good growth of cells and water purification still be obtained but at less satisfactory growth rates. In this example, the pump 37 maintained a pressure of 60 psi at 8 gallons per minute, and the unit proved capable of processing satisfactorily 90 gals. per hour at four times the ion concentration of normal municipal waste.

As an example of how the waste loading controller works, the system can operate on the basis of monitoring the phosphate content. Signals may be supplied at one or more of the stations 57, 61, and 72, indicating the phosphate content there. Thus, if the phosphate content at the stations 57, 61, and 72, or any one of them is lowered, meaning that the algae are consuming phosphate at too fast a rate, the monitor station 57, 61, or 72 sends to the waste loading controller 25 a signal to that effect, which is used there to send a signal to the waste loading monitor 10 to lower the density in the system, thereby reducing the nutrient uptake rate in the system. The waste loading monitor 10 may then signal the waste loading controller 25 to actuate the recycle valve 85 to increase the recycle rate, thereby establishing the correct density and rate of uptake.

As shown in FIG. 1, three similar tanks 14, 51, an 64 may be used in series, and the partially reacted mass from the tank 14 flows to the tank 51 where it is treated in the same manner as in the tank 14, then flows to the tank 64 where the same treatment is again applied. The average stay may be about fifteen minutes in each tank. Effluent from the tank 64 is completely reacted, as can be determined by ascertaining the total oxygen demand of the effluent, and is conducted to the settling tank 80, which preferably is kept dark, so that the algae product increases it specific gravity and thereby precipitates or settles out to a densified lower layer which is then centrifuged. The algae product is recovered from the centrifuge 81 and, except for what is recycled, can be spray dried or otherwise dried and is a good source of protein feed.

Clear water from the centrifuge 81 can be returned to natural waters or otherwise used. When added to natural waters it will have a purifying effect thereon because it is charged with excess oxygen developed by the algae during the growth thereof. In this system, a 50% to 80% reduction in doubling time of the cells has been obtained. For example, in some runs doubling time of Chlorella sp. was reduced from 5.8 to 2.2 hours in high density cultures of 140 grams per liter.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

I claim:

1. A method of growing substantially unicellular algae and simultaneously purifying biodegradable waste material containing aerobic bacteria, such as sewage after comminution and after removal of most particulate matter, including non-biodegradable matter and after being largely freed from turbidity so that light can effectively penetrate thereinto, to provide a clean water, comprising:

preparing an aqueous admixture of said algae and said waste material, said waste material providing nitrogen and phosphorous nutrients for said algae and being admixed in an amount to support growth thereof, aerating and agitating said admixture and supplying it with carbon dioxide and air in an amount that balances the bacterial growth with the algal growth to keep them in approximately the same relative proportions, circulating the agitated admixture in a series of many cycles where it is exposed at each cycle for a period of about one-half second to about two seconds to light capable of inducing photosynthesis and then is subjecting it to a longer period of darkness the algae being exposed to light for sufficient time and of such frequency and intensity to effect photosynthesis without excessive oxidation of thylakoids, which are inherently a part of algae, and then being exposed to dark for sufficient time to regenerate the thylakoids, to effect growth of algae and consumption of substantially all of said waste material, and separately recovering an algae product and a purified water effluent while recirculating some of said algae product.

said method being continuous, said admixture being maintained in a continuous culture state.

2. The method of claim 1 wherein said admixture is alternately exposed to darkness and light in a ratio of about 10:1.

3. The method of claim 1 wherein said admixture is exposed to light for a period of 0.9 to 1.2 seconds for each exposure.

4. The method of claim 1 wherein said admixture includes aerobic bacteria, which supplies part of the carbon dioxide and wherein aeration is done with a mixture of carbon dioxide and air in a ratio of oxygen to carbon dioxide of about 5 or 6 to 1, to maintain the growth rates of algae and bacteria in a balanced symbiotic condition wherein the algae weighs about twenty times as much as the bacteria.

5. The method of claim 1 wherein said light is artificial light supplied at a wavelength of about 440 to 680 nanometers, thereby preventing quenching effect on the 680 nm photosynthetic uptake of the algae cells, and an intensity of more than 400 foot candles.

6. The method of claim 1 wherein said aeration supplies the force for said circulating step and for thereby providing the alternation between light exposure and darkness.

7. The method of claim 6 wherein said waste is domestic sewage containing phosphate detergent.

8. The method of claim 1 wherein said algae admixture has a density of about 140 to 150 grams per liter, and a layer about 2.7 inches in depth is exposed to said light.

9. The method of claim 1 wherein said algae admixture product is settled, said settled admixture removed to recover separately the clean water and the algae product, said clean water subsequently being disinfected by bubbling ozone therethrough.

10. The method of claim 9 wherein said clean water is returned to natural waters.

11. The method of claim 1 wherein said algae are chosen from the group consisting of Chlorophyta, Euglenophyta, Christophyta, Pyrrophyta, Cyanophyta, and Rhodophyta.

12. The method of claim 11 wherein said algae are species of the genus Chlorella.

13. The method of claim 12 wherein said algae are Chlorella TX115.

14. The method of claim 12 wherein said algae are Chlorella pyrenoidosa.

15. The method of claim 11 wherein the algae are Porphyridium cruentum to provide carotene-bearing algae product.

16. The method of claim 11 wherein said algae are Scenedesmus obliquus.

17. A method for rapidly growing unicellular algae and the like using nutrient wastes from sewage, after comminution of said sewage, removal of nonbiodegradable and large particles therefrom and reduction of turbidity thereof, comprising:

continuously mixing the algae and wastes in water, with aerobic bacteria present in said wastes, said wastes being continuously supplied balancing the oxygen and carbon dioxide requirements of the mixture to maintain a desired symbiotic relationship between the algae and the bacteria, continuously flowing a shallow layer of the mixture beneath light of wavelength and intensity able to trigger photosynthesis in said algae for a light exposure of said shallow layer to its full depth for between one-half second and two seconds and then into a darkened zone for a much longer time, the light and darkness being alternated many times to effect growth of the algae and consumption of substantially all of said waste, and continuously separating and recovering an algae product and a purified water product.

18. The method of clam 17 wherein said algae are chosen from the group consisting of Chlorophyta, Euglenophyta, Christophyta, Pyrrophyta, Cyanophyta, and Rhodophyta.

19. The method of claim 17 wherein the mixture is continuously agitated, circulated between light and dark, and aerated during the flowing steps by a gaseous mixture of carbon dioxide and of air in a ratio of oxygen to carbon dioxide of about 5 or 6 to 1, to maintain a stable ratio of algae to bacteria.

20. The method of claim 17 wherein the mixture is exposed to darkness about ten times as much as it is exposed to light.

21. The method of claim 20 wherein each exposure to light is for a period of about one second.

22. A device adapted to growth of an algae product and purification of aqueous wastes, comprising in combination:

a stationary, generally rectangular, opaque tank having a base, a first and a second side wall and two end walls, and being open at the top for exposure to light, said first side wall being in the form of a curved section generally shaped like the curve generated by translation of a parabola, injector means disposed in said base opposite said first side wall, horizontal baffle means disposed well in the upper portion of said tank and spaced downwardly from said top so as to divide the tank into a thin upper portion above said baffle means and a much larger portion below said baffle, and means for injecting fluid through said injector means into said tank toward said first side wall to impel fluid to move up said first side wall with a lenticular flow and to flow over said baffle means and back therebelow, the flow over said baffle means providing exposure to light and the flow therebelow resulting in exposure to darkness much longer in time than the exposure to light.

23. The device of claim 22 having fluorescent light tube means supported by said tank above said tank and over said baffle.

24. A device as in claim 22 wherein said injector means comprises a series of aerating injectors.

25. A device as in claim 24 wherein said injectors are horizontally disposed and are arranged perpendicularly with respect to said first side wall.

26. A device as in claim 24 wherein some of said injectors are connected to a gas inlet means.

27. A device as in claim 24 wherein each said wall and said baffle has a black interior surface.

28. A device as in claim 24 wherein said baffle has a light-reflective upper surface.

29. A device adapted to growth of an algae product and purification of aqueous wastes, comprising in combination:

a tank having a base, a first and a second side wall and two end walls, and being open at the top, said first side wall being in the form of a section of a parabolic curve, injector means disposed in said base opposite said first side wall, horizontal baffle means disposed well in the upper portion of said tank and spaced downwardly from said top, and means for injecting fluid through said injector means into said tank toward said first side wall, some of said injector means being connected to a means disposed at said second side wall adapted to collect foam from the upper end of said tank.

30. A system for producing clean water and an algae product high in protein which comprises:

a reaction zone, means to introduce algae into said zone, means to continuously introduce liquid organic waste material and aerobic bacteria into said zone to provide nitrogen and phosphorus nutrients for said algae, means to introduce at least one gas chosen from the group consisting of air and carbon dioxide into said reaction zone to admix and agitate said algae and said waste materials to form a biomass and for maintaining a desired balance between said algae and bacteria, means to circulate a portion of said biomass in a shallow, illuminated path so that said biomas is exposed to light of sufficient intensity and of suitable frequency for about one-half second to two seconds followed by a considerably longer period of darkness, the periods of light and darkness alternating to effect growth of algae and consumption of said waste materials, means to withdraw reacted materials from said zone and separately recover algae product and clean water, and means to recirculate some of said algae product to said means to introduce algae.

31. The system of claim 30 wherein said means to circulate exposes said biomass to light for about one second at each path and then subjects it to darkness for about ten seconds.

32. A device adapted to growth of an algae product and purification of aqueous wastes comprising:

an opaque tank having an open upper end, means providing photosynthetic light above said open upper end, a horizontal baffle disposed in the upper portion of said tank and spaced downwardly a short distance from said open upper end so that most of said tank lies directly below said baffle and in darkness, being shielded from said light by said baffle, and means to circulate an aqueous mixture of said algae and aqueous waste first across over said baffle and then down below said baffle, and then back across over said baffle and so on for several circulation cycles, thereby providing short periods of light followed by longer periods of darkness between successive periods of light.

33. The device of claim 32 wherein said baffle is located such that about one-tenth of the contents of the tank lie above it and are exposed to said light and about nine-tenths of the contents of the tank lie below it and are shielded from the light.

34. The device of claim 32 wherein the sides of the baffle and the tank walls are curved to give a good flow pattern.

35. A device adapted to growth of an algae product and purification of aqueous wastes comprising:

a tank having an open upper end, means providing photosynthetic light above said open upper end, a horizontal baffle disposed in the upper portion of said tank and spaced downwardly a short distance from said open upper end, means to circulate an aqueous mixture of said algae and aqueous waste across over said baffle and down below said baffle, thereby providing short periods of light followed by longer periods of darkness between successive periods of light, a plurality of injectors at the lower end of the tank, horizontally disposed and facing a first side wall of said tano, gas inlet means connected to some of said injectors, and a means disposed at a second side wall of said tank for collecting foam from above said baffle and conveying it to other said injectors.

36. The device of claim 35 having means for spraying liquid across the upper end of said tank toward said means for collecting foam.

37. A continuous system for producing clean water and an algae product high in protein which comprises:

a. a reaction zone, b. means for continuously introducing algae into said zone, c. means for continuously introducing organic waste material with aerobic bacteria into said zone to provide nitrogen and phosphorus nutrients for said algae, d. means for continuously introducing controlled amounts of at least one gas selected from the group consisting of air and carbon dioxide into said reaction zone to admix and agitate said algae and said waste materials to form a biomass and to keep said algae and bacteria in a desired balance, e. means for continuously circulating a portion of said biomass in an illuminated path so that said bromass in exposed to a large series of limited alternate exposures to light of about one-half second to about two seconds each and to darkness for substantially longer times, to effect the growth of algae and consumption of said waste materials, f. means for continuously withdrawing reacted materials from said zone, g. means for centinuously and separately recovering algae product and clean water, h. means for circulating some of said algae product to step (b).

38. The system of claim 37 having means for continuously governing the introduction of algae and waste in steps (b) and (c) according to the quality of the reacted materials withdrawn in step (f).

39. A device adapted to growth of an algae product and purification of aqueous wastes, comprising in combination:

a generally rectangular, opaque tank having a base, a first and a second side wall and two end walls, and being open at the top for exposure to photosyn thetic light means thereabove, said first side wall being curved outwardly in vertica section to induce lenticular flow, injector means disposed in said base opposite said first side wall, horizontal baffle means spaced downwardly from said top and disposed well in the upper portion of said tank, so that most of said tank lies directly below said baffle means and is shielded from exposure to light thereby, and means for injecting fluid through said injector means into said tank toward said first side wall for lenticular flow up said first side wall and over said horizontal baffle means for a short exposure to light and then down into said tank at said second side wall for a longer exposure to darkness and then again over said baffle means in a continuing cycle.

40. A method comprising culturing unicellular algae and bacteria at a substantially constant growth and nutrient uptake rate by applying to a mixture of algae and bacteria in water light of photosynthetic frequencies at an intensity sufficient for adequately triggering photosynthesis, for regular periods between about one-half second and about two seconds each in duration, alternating with regular periods of darkness sufficiently long to enable regeneration of the photoreceptors to take place, so that the predominant number of individual algae cells are maintained in a uniform state with no aging and without excess formation of lipids, said culturing being provided with a continuous supply of light transmitting nutrient-bearing liquid wastes in sufficient quantity and at such a rate that
1. the mixture does not become nutrient-limiting to the microorganisms in the culture, and
2. said mixture removes sufficient quantities of said nutrients that the liquid of said wastes causes no harmful degradation of aquatic environment in which said liquid may be discharged after treatment, said algae being periodically withdrawn, and a portion of same is recycled to make up said mixture.

* * * * *